United States Patent
Kawasaki et al.

(10) Patent No.: US 8,040,519 B2
(45) Date of Patent: Oct. 18, 2011

(54) BIOLOGICAL OPTICAL MEASUREMENT APPARATUS

(75) Inventors: Shingo Kawasaki, Tokyo (JP); Kimitaka Anami, Nishitokyo (JP)

(73) Assignee: Hitachi Medical Corporation, Tokyo (JP)

( * ) Notice: Subject to any disclaimer, the term of this patent is extended or adjusted under 35 U.S.C. 154(b) by 449 days.

(21) Appl. No.: 12/301,819

(22) PCT Filed: May 18, 2007

(86) PCT No.: PCT/JP2007/060232
§ 371 (c)(1), (2), (4) Date: Nov. 21, 2008

(87) PCT Pub. No.: WO2007/135993
PCT Pub. Date: Nov. 29, 2007

(65) Prior Publication Data
US 2010/0245828 A1 Sep. 30, 2010

(30) Foreign Application Priority Data
May 23, 2006 (JP) .................................. 2006-142913

(51) Int. Cl.
*G01N 21/55* (2006.01)
*G06K 9/00* (2006.01)
*A61B 5/00* (2006.01)

(52) U.S. Cl. ......... 356/445; 600/473; 600/476; 382/134
(58) Field of Classification Search .................. 356/445, 356/246, 625–636; 600/310, 476, 473, 424, 600/427; 382/134
See application file for complete search history.

(56) References Cited

U.S. PATENT DOCUMENTS

| | | | |
|---|---|---|---|
| 5,803,909 A * | 9/1998 | Maki et al. | 600/310 |
| 6,352,509 B1 * | 3/2002 | Kawagishi et al. | 600/443 |
| 6,516,209 B2 * | 2/2003 | Cheng et al. | 600/323 |
| 6,542,763 B1 * | 4/2003 | Yamashita et al. | 600/310 |
| 6,591,130 B2 * | 7/2003 | Shahidi | 600/424 |
| 6,904,302 B2 * | 6/2005 | Hirabayashi et al. | 600/344 |
| 6,947,779 B2 * | 9/2005 | Yamamoto et al. | 600/323 |
| 7,039,454 B1 * | 5/2006 | Kaga et al. | 600/476 |
| 7,065,392 B2 * | 6/2006 | Kato | 600/323 |
| 7,228,166 B1 * | 6/2007 | Kawasaki et al. | 600/476 |
| 7,613,502 B2 * | 11/2009 | Yamamoto et al. | 600/473 |

FOREIGN PATENT DOCUMENTS

| | | |
|---|---|---|
| JP | 09-019408 | 1/1997 |
| JP | 2000-171390 | 6/2000 |
| WO | WO 2006/009178 A1 | 1/2006 |

* cited by examiner

*Primary Examiner* — Sang Nguyen
(74) *Attorney, Agent, or Firm* — Antonelli, Terry, Stout & Kraus, LLP.

(57) ABSTRACT

A biological optical measurement apparatus including an applied unit having plural light irradiating probes for irradiating an object with light and plural light detecting probes for detecting light returning from the object, and worn by the object, a measuring unit for measuring the amount of light detected by the light detection probes, a two-dimensional image constructing unit for constructing two-dimensional topographic images from the measurement result of the detected light amount, and a monitor for displaying the two-dimensional topographic images, is further equipped with a three-dimensional image constructing unit for making the two-dimensional topographic images correspond to measurement positions and superposing the two-dimensional topographic images in order of measurement time to thereby construct a three-dimensional image, the thus-constructed three-dimensional image being displayed on the monitor.

17 Claims, 15 Drawing Sheets

BIOLOGICAL OPTICAL MEASUREMENT APPARATUS

TECHNICAL FIELD

The present invention relates to a biological optical measurement apparatus for measuring an optical characteristic of an object to be examined by using light.

BACKGROUND ART

In a conventional biological optical measurement apparatus, an intensity signal of detected light is displayed as a topographic image on a two-dimensional display screen representing measurement positions. The topographic image is created by measuring a time integration value (or time average value) of a relative variation amount of a measured hemoglobin concentration and linearly interpolating a value between respective measurement points (for example, see Patent Document 1).

Patent Document 1: JP-A-9-19408

DISCLOSURE OF THE INVENTION

Problem to be Solved by the Invention

In the conventional biological optical measurement apparatus as described above, a topographic image is created every measurement time. Accordingly, the variation amount of the hemoglobin concentration at some time can be spatially recognized, however, it is difficult to visually recognize the temporal behavior of the variation amount of the hemoglobin concentration.

The present invention has been implemented to solve the foregoing problem, and has an object to provide a biological optical measurement apparatus that can facilitate visual recognition of a time-variation of measurement result information.

Means of Solving the Problem

A biological optical measurement apparatus according to the present invention which comprises an applied unit which has plural light irradiation probes for irradiating an object with light and plural light detection probes for detecting light returning from the object, and which is worn by the object, a measuring unit for measuring the amount of light detected by the light detection probes, a two-dimensional image constructing unit for constructing two-dimensional topographic images from the measurement result of the detected light amount, and a monitor for displaying the two-dimensional topographic images, is equipped with a three-dimensional image constructing unit for making the two-dimensional topographic images correspond to measurement positions and superposing the two-dimensional topographic images in order of measurement time to thereby construct a three-dimensional image, the thus-constructed three-dimensional image being displayed on the monitor.

BEST MODES FOR CARRYING OUT THE INVENTION

Best modes for carrying out the invention will be described with reference to the drawings.

First Embodiment

Figure 1:
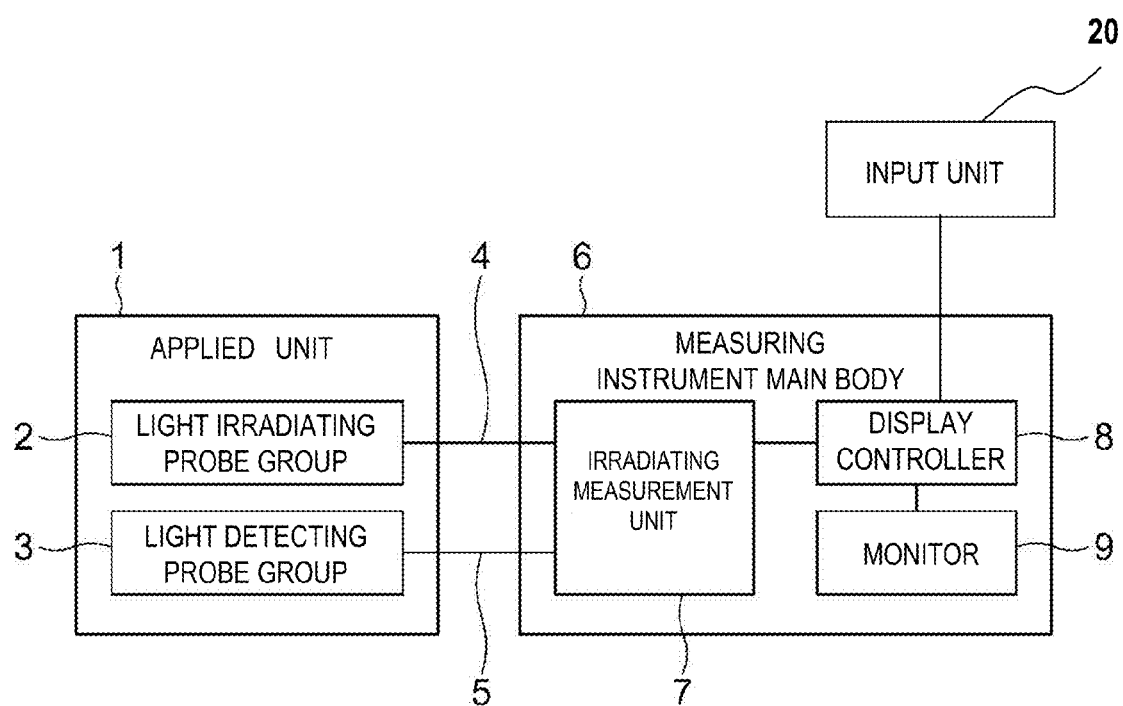
FIG. 1 is a block diagram showing the construction of a biological optical measurement apparatus according to a first embodiment of the present invention.

FIG. 1 is a block diagram showing the construction of a biological optical measurement apparatus according to a first embodiment of the present invention. An application 1 mounted on an object has a light irradiating probe group 2, a light detecting probe group 3 and a holder (not shown) for holding the probe groups 2 and 3. The light irradiating probe group 2 contains plural light irradiating probes for irradiating an object with light. The light detecting probe group 3 contains plural light detecting probes for detecting light returning from the object. The light irradiating probes and the light detecting probes are arranged in a matrix form on the holder. The light irradiating probes and the light detecting probes are alternately arranged.

The applied unit 1 is connected to a measurement instrument main body 6 through an irradiating optical fiber group 4 containing plural irradiating optical fibers and a detecting optical fiber group 5 containing plural detecting optical fibers.

The measurement instrument main body 6 has an irradiating measurement unit 7, a display controller 8, a monitor 9 and an input unit 9.

Figure 15:
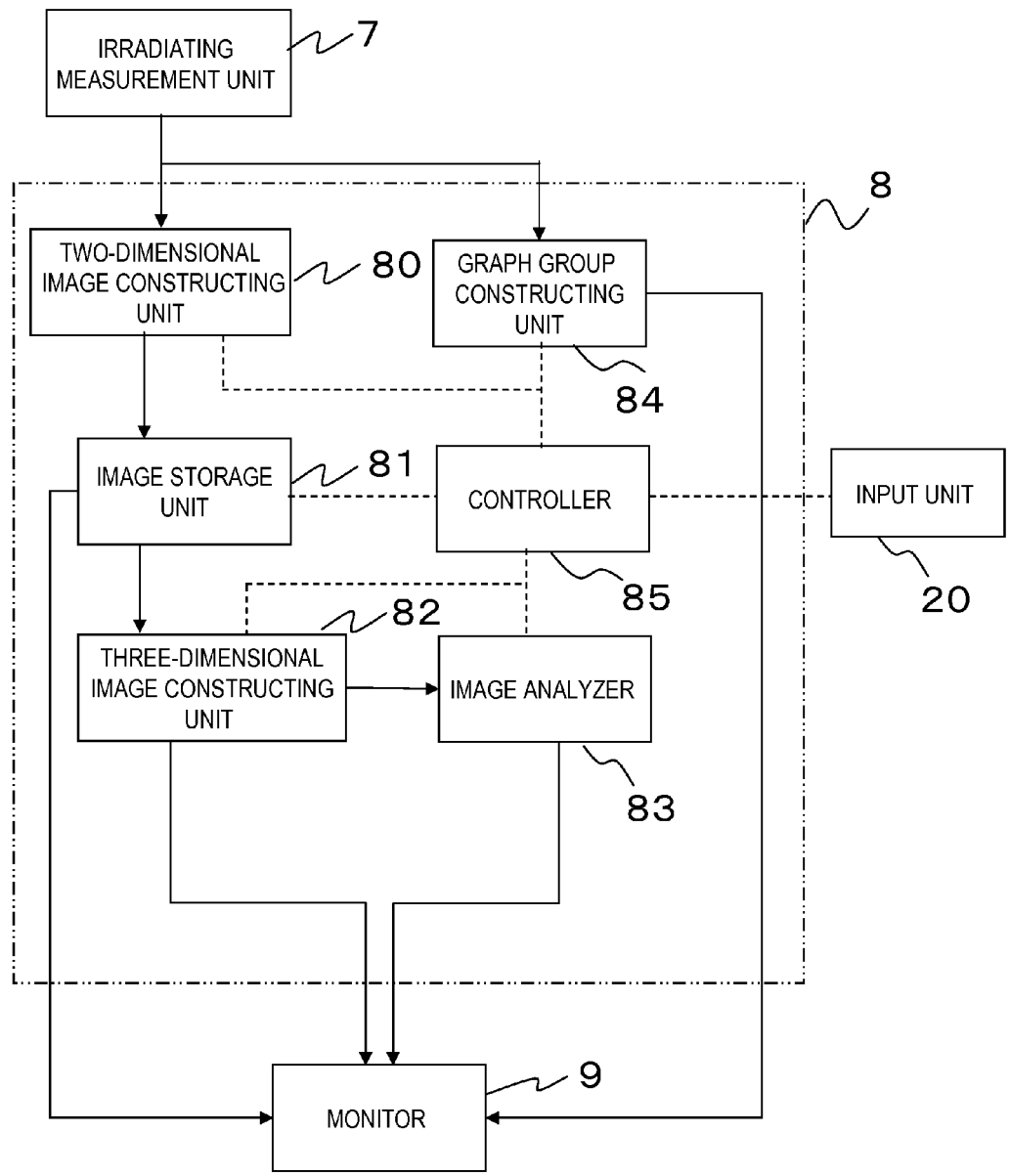
FIG. 15 is a block diagram showing the construction of a display controller of the present invention.

The irradiating measurement unit 7 generates light of wavelengths from the visible region to the infrared region and transmits the light to the light irradiation probe group 2, and also measures the amount of detected light at each light detecting probe. The irradiating measurement unit 7 determines, for example, the variation amount of hemoglobin concentration in blood as the measurement result information corresponding to the measurement result of the detected light amount. The display controller 8 displays the measurement result information determined in the irradiation measurement unit 7 as an image on the monitor 9. The input unit 9 makes an instruction concerning image display to the display controller 8. As shown in FIG. 15, the display controller 8 comprises a two-dimensional image constructing unit 80, an image storage unit (ROM, RAM and a hard disk or the like) 81, a three-dimensional image constructing unit 82, an image analyzer 83, a graph group constructing unit 84 and a controller 85. The controller 85 is connected to the input unit 9, and controls the respective constituent elements of the display controller 8 on the basis of input information from the input unit 9. The two-dimensional image constructing unit 80 creates two-dimensional topographic images on the basis of the variation amount and measurement position of hemoglobin concentration measured by the irradiating measurement unit 7. The image storage unit 81 stores two-dimensional topographic images created in the two-dimensional image constructing unit 80 in order of measurement time. The three-dimensional image constructing unit 82 superposes the two-dimensional topographic images stored in the image storage unit 81 in the time-axis direction in order of the measurement time to construct a three-dimensional image. The three-dimensional constructing unit displays the constructed three-dimensional image on the monitor 9. The image analyzer 83 analyzes parameters such as the time, etc. on the basis of the shape and distribution of the three-dimensional image, and displays the analysis result on the monitor 9.

Figure 2:
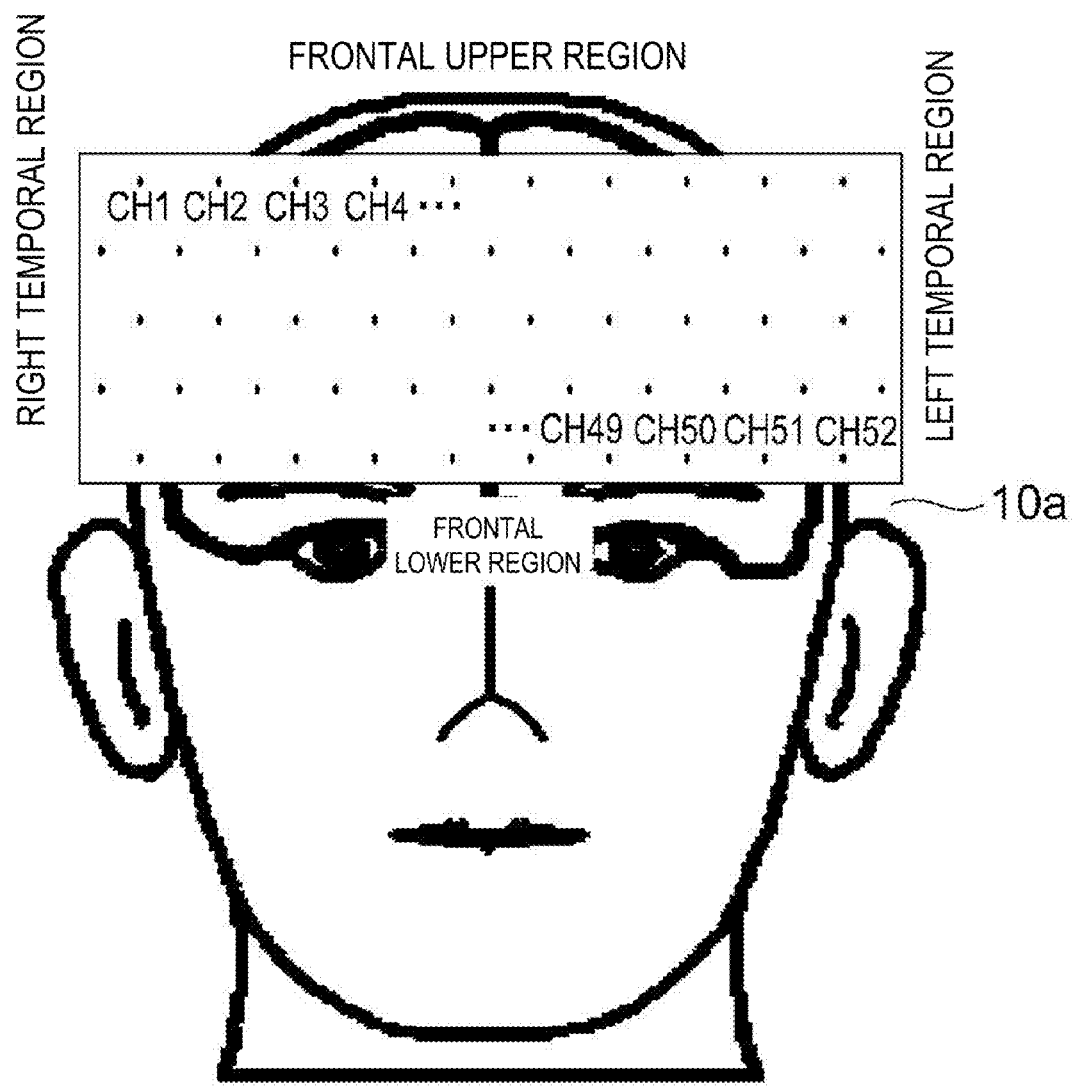
FIG. 2 is a diagram showing an example of a body mark displayed on a monitor of FIG. 1.

In addition to the measurement result information, a body mark 10a as shown in FIG. 2 is displayed on the monitor 9. The body mark storage unit (not shown) creates and stores plural body marks which schematically show the arrangement state of the measurement positions (measurement points) in advance. An operator selects one of the body marks stored in the body mark storage unit through the input unit 20 and the controller 85, and displays the selected body mark on the monitor 9. The body mark 10a of FIG. 2 represents that the measurement area is the frontal region. Furthermore, in this example, 52 measurement positions corresponding to channel 1 to channel 52 are provided.

Each measurement position is located between the light irradiating probe and the light detecting probe. A part of light irradiated from the light irradiating probe is transmitted through brain cortex at a measurement position and then incident to the light detecting probe. At this time, the detected light amount at the light detecting probe varies in accordance with the hemoglobin concentration at the measurement position. Accordingly, The relative variation of the hemoglobin concentration can be measured from the variation of the detected light amount. Furthermore, by displaying the body mark on the monitor 9 together with the measurement result information, the schematic corresponding relationship between the measurement result and the measurement position can be grasped.

Figure 3:
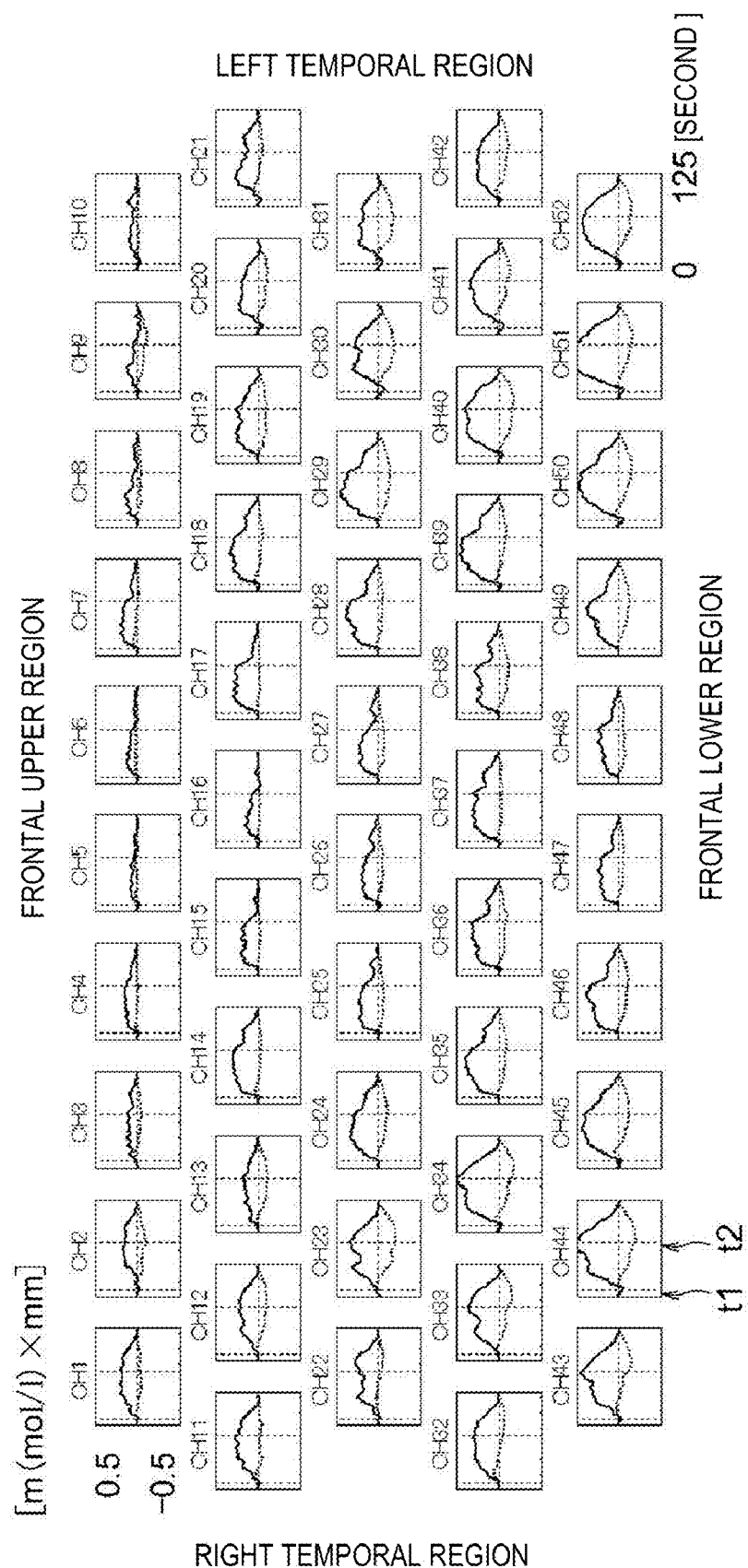
FIG. 3 is a diagram showing an example of a graph display of measurement result information based on an irradiating and measuring unit of FIG. 1.

Furthermore, on the basis of the measurement result information corresponding to the measurement result of the detected light amount obtained from the irradiating measurement unit 7, the graph group constructing unit 84 constructs a graph group in which graphs representing the time variations of the hemoglobin concentration (measurement values) at the respective measurement positions are arranged in connection with the measurement positions respectively. As shown in FIG. 3, the graph group constructing unit 84 displays this graph group on the monitor 9. In the example of FIG. 3, the measurement area corresponds to the frontal region. In each group, the abscissa axis represents the time, and the ordinate axis represents the hemoglobin concentration. Furthermore, the relative variation amount from the measurement start time point is shown as the hemoglobin concentration. Furthermore, in each graph, a solid line represents the oxygenated hemoglobin concentration, and a broken line represents the reduced hemoglobin concentration. In this example, a word recall problem is given to an object at a measurement time, and a word recall problem start time (t1) and a word recall problem finish time (t2) are represented by broken lines in each graph.

Here, the word recall problem is one of test methods disclosed in "Suto T, Fukuda M, Ito M, Uehara T, Mikuni M(2004) Multi-channel near-infrared spectroscopy in depression and schizophrenia: cognitive brain activation study. Biol Psychiatry 55: 501-511, and it is a problem for making the object recall various words and utter a sound thereof. As is shown in FIG. 3, the oxygenated hemoglobin increases at the same time as the start time of the word recall problem in many channels, and reduces at the same time as the finish time of the word recall problem.

Figure 4:
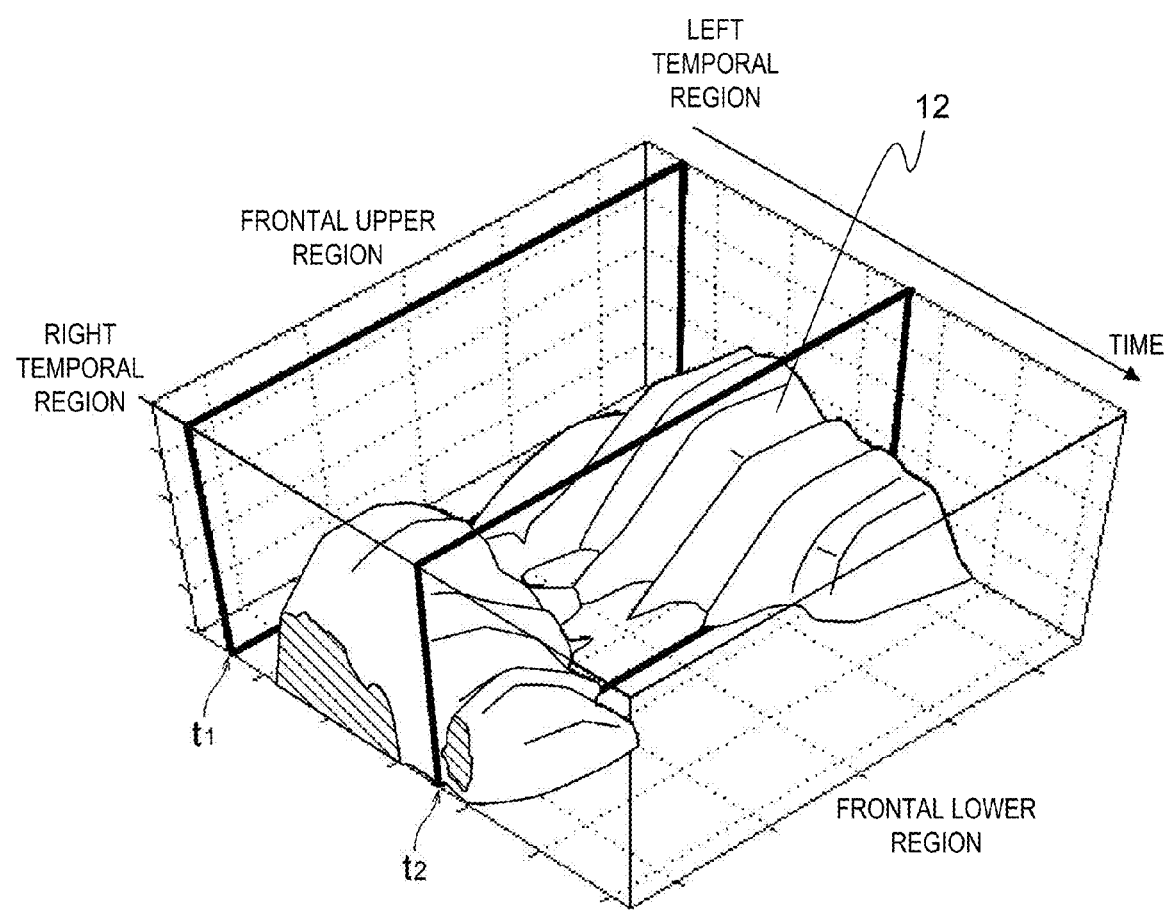
FIG. 4 is a diagram showing an example in which the measurement result information of the irradiating and measuring unit of FIG. 1 is displayed as a three-dimensional image.

Next, FIG. 4 is a diagram showing an example in which the measurement result information of the irradiating measurement unit 7 of FIG. 1 is displayed as a three-dimensional image. The three-dimensional image is displayed as a rectangular parallelepiped obtained by superposing rectangular hemoglobin concentration distribution diagrams corresponding to the measurement areas in the time-axis direction. Furthermore, in this example, increase/decrease of the oxygenated hemoglobin concentration is represented by color shading, and also variations which are less than a predetermined threshold value are neglected and regarded as being transparent. Accordingly, the three-dimensional image contains a transparent portion in which variation of the oxygenated hemoglobin concentration is small and an activated portion 12 in which variation of the oxygenated hemoglobin concentration is large.

Figure 5:
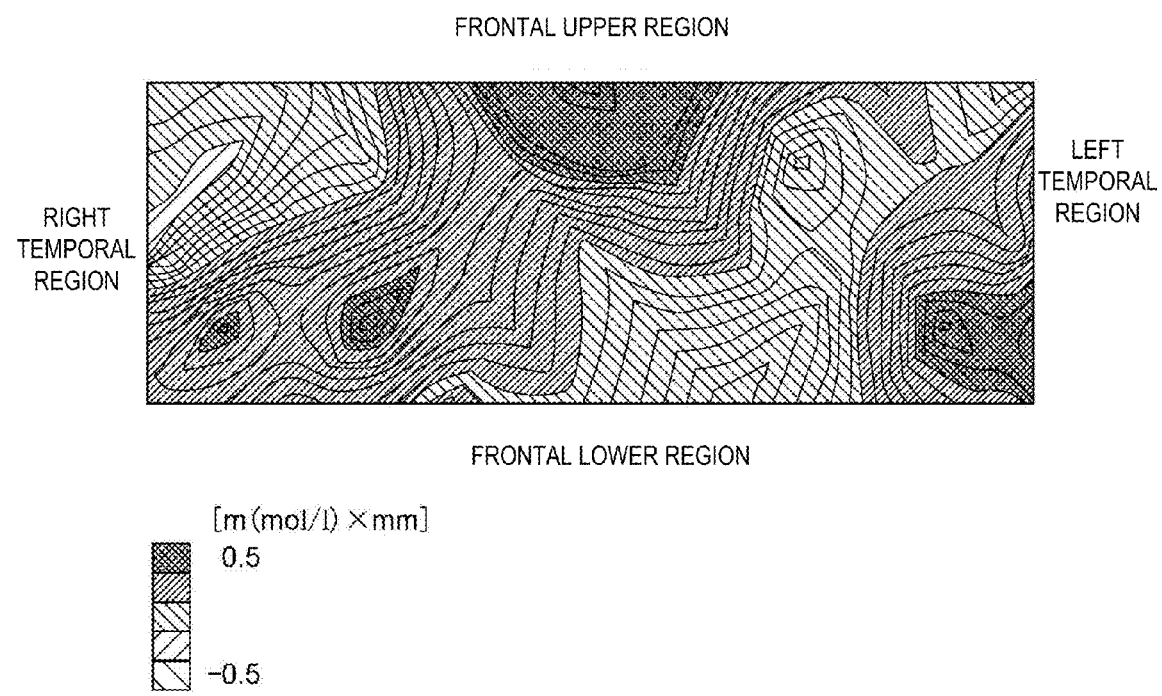
FIG. 5 is a diagram showing an example of a two-dimensional topographic image created by a display controller of FIG. 1.

A method of creating a three-dimensional image by the display controller 8 will be described. In the following description, it is assumed that the measuring area corresponds to a frontal region, however, the same creating method is also used for other measuring areas. FIG. 5 is a diagram showing an example of a two-dimensional topographic image (contour image) created by the two-dimensional image constructing unit 80 of FIG. 15. The two-dimensional image constructing unit 80 interpolates data between adjacent measurement positions (between measurement channels) on the basis of the measurement result information at some time which is obtained from the irradiation measurement unit 7, thereby creating the two-dimensional topographic image as shown in FIG. 5. Then, the two-dimensional topographic image is stored in the image storage unit 81. The two-dimensional topographic image is output from the image storage unit 81 to the monitor 9 and displayed on the monitor 9.

In FIG. 5, the increase/decrease of the oxygenated hemoglobin concentration after 10 seconds from the start of the word recall problem is represented by color shading. The increase and decrease of hemoglobin may be represented by different colors (for example, the increase is represented by red and the decrease is represented by blue). It is apparent that hemoglobin increases in a dark area of FIG. 5 and decreases in a light area.

Figure 6:
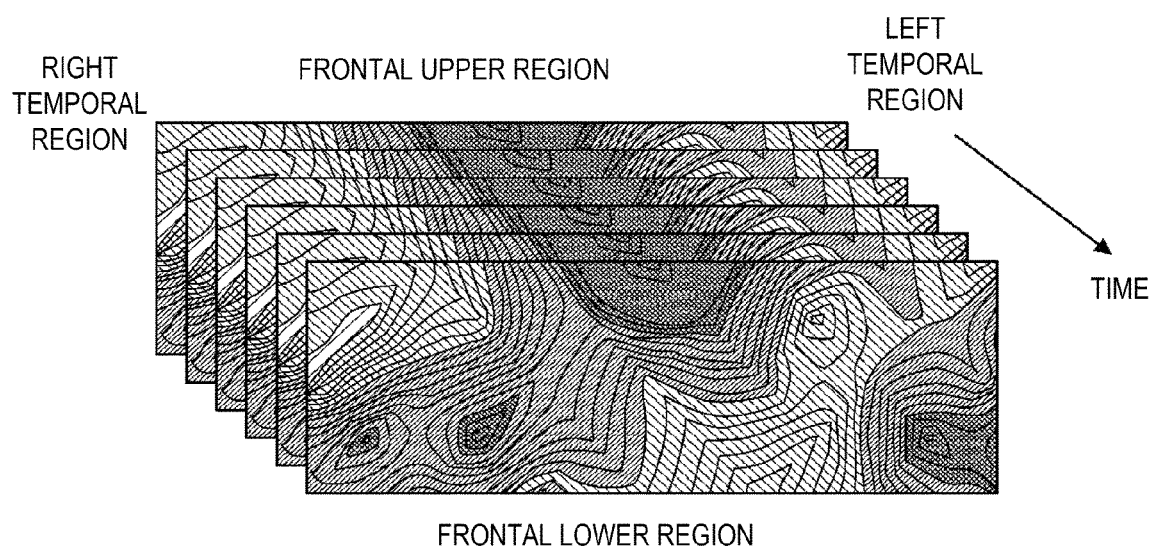
FIG. 6 is a diagram showing a state that two-dimensional topographic images as shown in FIG. 5 are superposed in a time-axis direction in order of measurement time.
Figure 7:
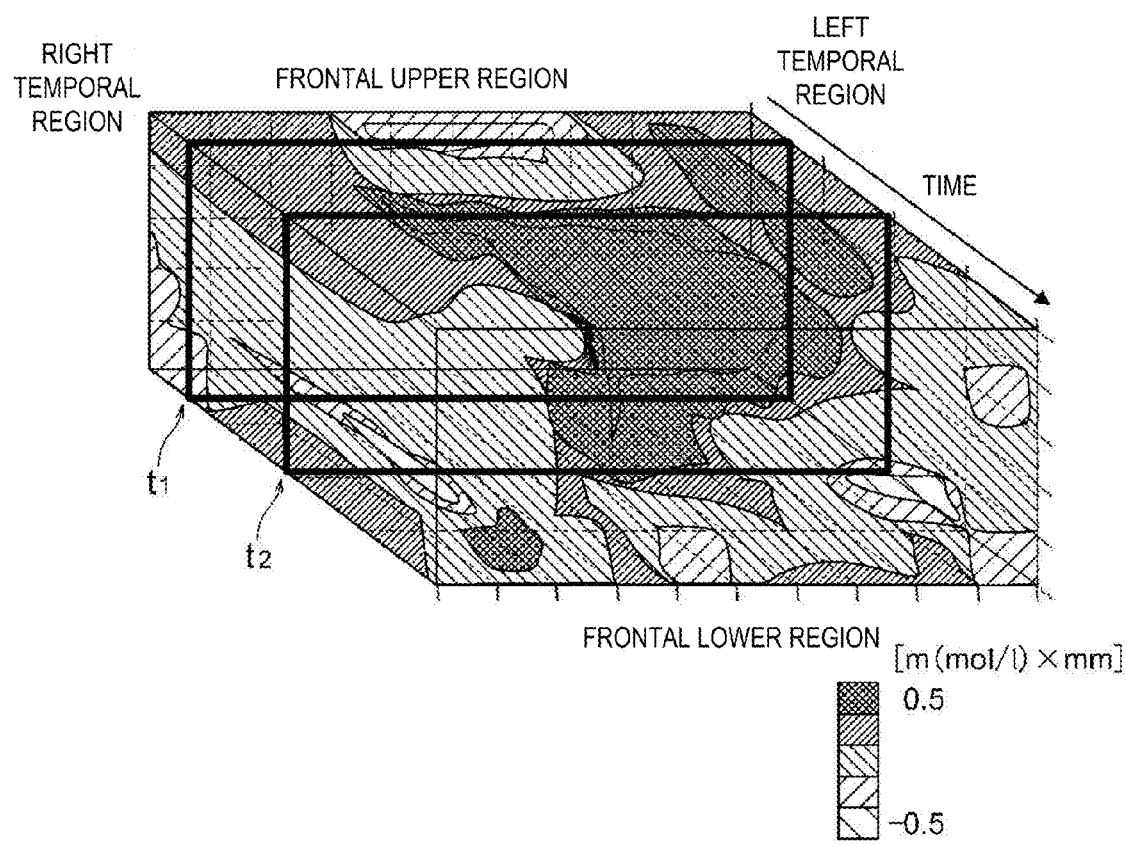
FIG. 7 is a diagram showing a state that the adjacent two-dimensional topographic images of FIG. 6 are subjected to interpolation.

FIG. 6 is a diagram showing a state that two-dimensional topographic images stored in the image storage unit 81 as shown in FIG. 5 are superposed in the time-axis direction in order of measurement time, and FIG. 7 is a diagram showing a state that adjacent two-dimensional topographic images of FIG. 6 are interpolated. The three-dimensional image constructing unit 82 successively reads out the two-dimensional topographic images from the image storage unit 81 every 0.1 second in order of measurement time, and ten two-dimensional topographic images are superposed every one second. Through the processing of FIGS. 5 to 7, the three-dimensional image constructing unit 82 outputs a three-dimensional image to the monitor 9, and displays this three-dimensional image on the monitor 9. The reading interval of the two-dimensional topographic image may be arbitrarily set by the input unit 20. The reading interval information set in the input unit 20 is output to the three-dimensional image constructing unit 82, and the three-dimensional image constructing unit 82 superposes the two-dimensional topographic images on the basis of the input reading interval information. For example, when the volume of a constructed three-dimensional image is measured, the three-dimensional image constructing unit 82 reads out a two-dimensional topographic image every 0.02 second, and fifty two-dimensional topographic images are superposed every one second, thereby constructing the three-dimensional image.

As described above, the variation amount of hemoglobin concentration is displayed within a plane corresponding to a measurement area in connection with the measurement position to obtain an image (two-dimensional topographic image), and the three-dimensional image constructing unit 82 superposes these images (the two-dimensional topographic images) in the time-axis direction in order of measurement time, thereby creating a three-dimensional image (three-dimensional topographic image) and displaying it on the monitor 9. At this time, the three-dimensional image constructing unit 82 creates a three-dimensional image while adjacent measurement result information is interpolated with respect to the measurement position and the measurement time.

Furthermore, the three-dimensional image constructing unit 82 can arbitrarily set the threshold value of the measurement result information, and one of display and non-display of the measurement result information can be selected with the input unit 20 with respect to the set threshold value as the boundary. For example, in FIG. 4, the threshold value is set to 0.1 [m(mol/1)×mm], an area in which the variation amount of the hemoglobin concentration is above the threshold value of 0.1 is color-displayed as the activated portion 13, and a site in which it is less than the threshold value is transparent (non-displayed). As the display method of setting the threshold value as described above may be adopted a method of color-displaying only a site which is not more than the threshold value. A method of displaying areas with difference colors with respect to the threshold value as the boundary may also be adopted.

Figure 8:
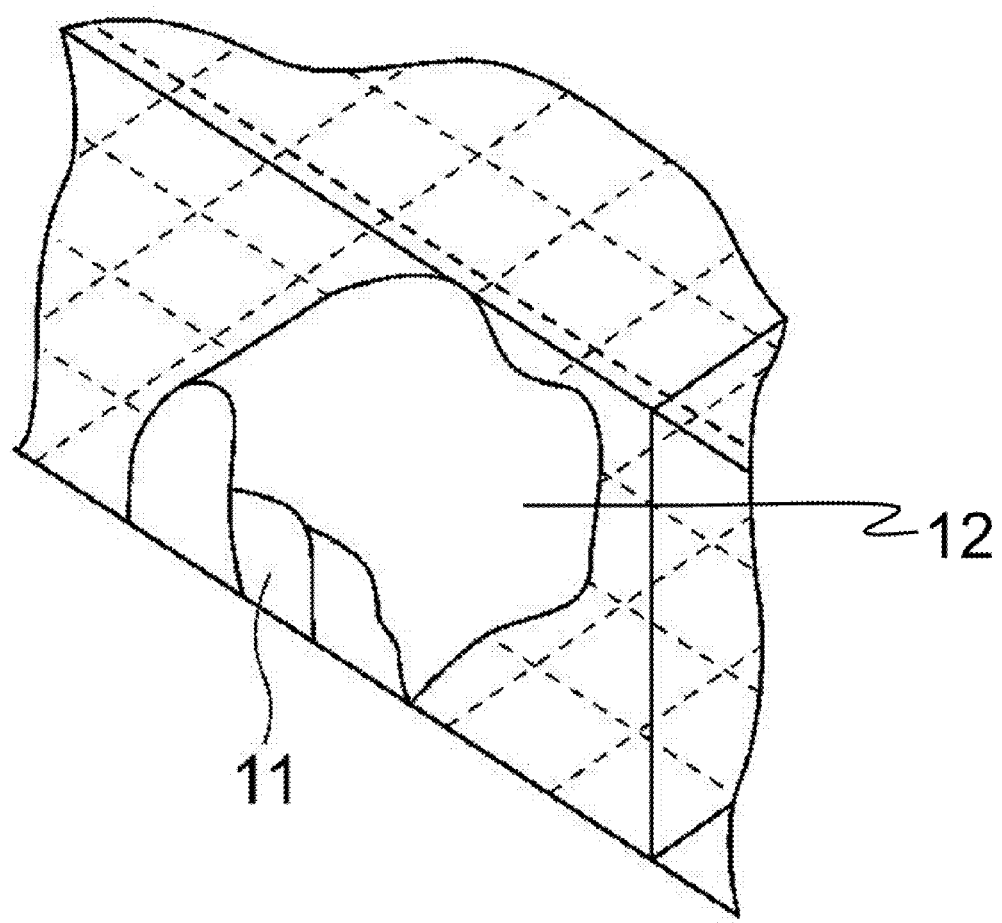
FIG. 8 is a diagram showing an example in which an opaque three-dimensional image is displayed on the monitor of FIG. 1.
Figure 9:
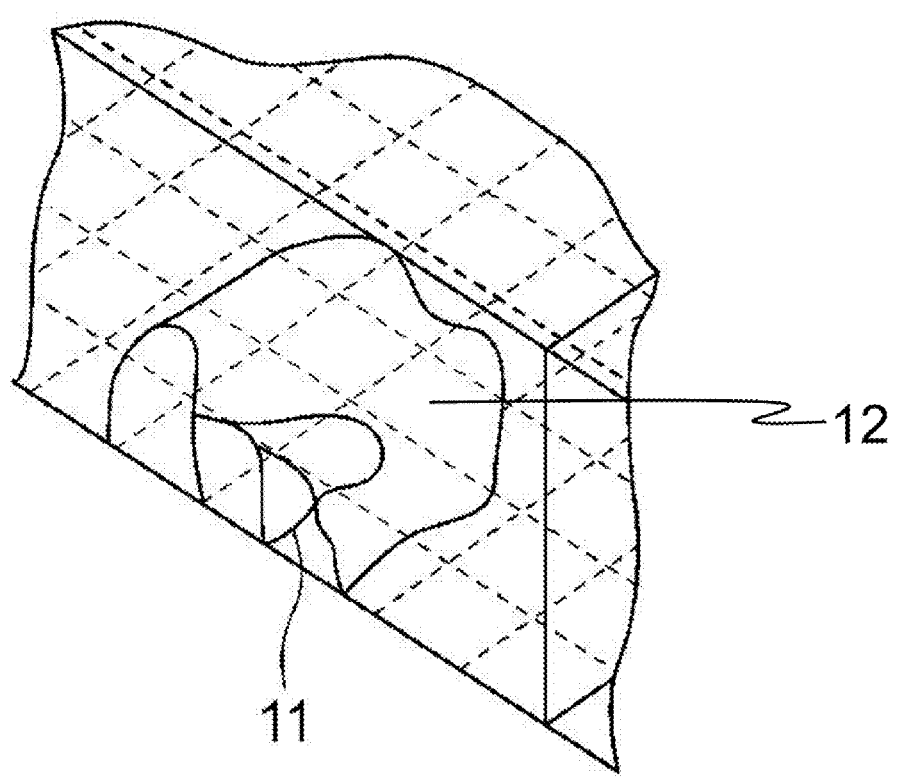
FIG. 9 is a diagram showing an example in which the three-dimensional image of FIG. 8 is displayed at a predetermined clarity.
Figure 10:
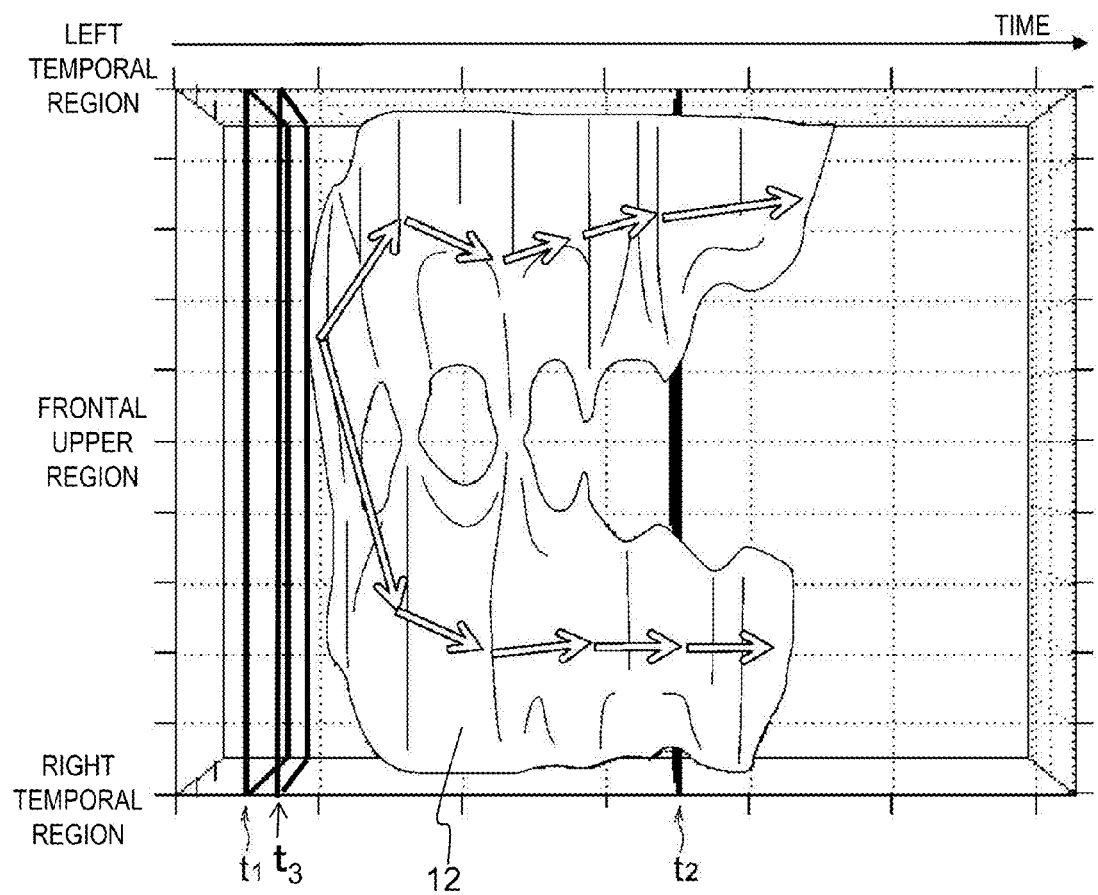
FIG. 10 is a diagram showing a display state when the three-dimensional image of FIG. 4 is viewed downwardly from the frontal upper portion.

Furthermore, by inputting the degree of transparency at the input unit 20, the activated portion 12 in the three-dimensional image can be displayed by the three-dimensional image constructing unit 82 at the degree of transparency concerned. FIG. 8 is a diagram showing an example in which the opaque activated portion 12 is displayed on the monitor 9 of FIG. 1, and FIG. 9 is a diagram showing an example in which the activated portion 12 of FIG. 10 is displayed at a predetermined degree of transparency. By selecting the display method shown in FIG. 9, a void/tunnel portion 11 (a portion having no variation in hemoglobin concentration) in the activated portion 12 can be easily recognized. The degree of transparency can be freely adjusted. Furthermore, as a method of displaying the void/tunnel portion 11 may be adopted a reversing display method in which a portion varying in hemoglobin concentration is made transparent and a portion 11 having no variation of hemoglobin concentration is colored.

Furthermore, by inputting any angle through the input unit 20, a three-dimensional image can be displayed by the three-dimensional image constructing unit 82 at the input angle. For example, FIG. 10 is a diagram showing a display state when the three-dimensional image of FIG. 4 is viewed in the downward direction from the upper portion of the frontal region. The rotation of the three-dimensional image may be freely executed, and it may be displayed upwardly from the lower portion of frontal region or from the right or left temporal region.

Furthermore, by inputting color information through the input unit 20, the time zone area from the problem start (t1) to the problem end (t2) can be displayed by the three-dimensional image constructing unit 82 using a color different from colors before the start of the problem and after the end of the problem.

Furthermore, the three-dimensional image constructing unit 82 may execute lighting on a three-dimensional image as shown in FIG. 4 to add shade and shadow to the activated portion 12. The position, irradiation direction and brightness of a light source for the lighting may be freely set by the input unit 20.

Plural arrows provided to the three-dimensional image of FIG. 10 represent the moving direction of the activated site of blood. The three-dimensional image constructing unit can provide such arrows (stream line). The three-dimensional image constructing unit 82 creates the arrows as shown in FIG. 10 by linking the peak positions of the hemoglobin concentration at respective times. The transition of the blood amount variation can be checked by the direction and length of the arrows.

Figure 11:
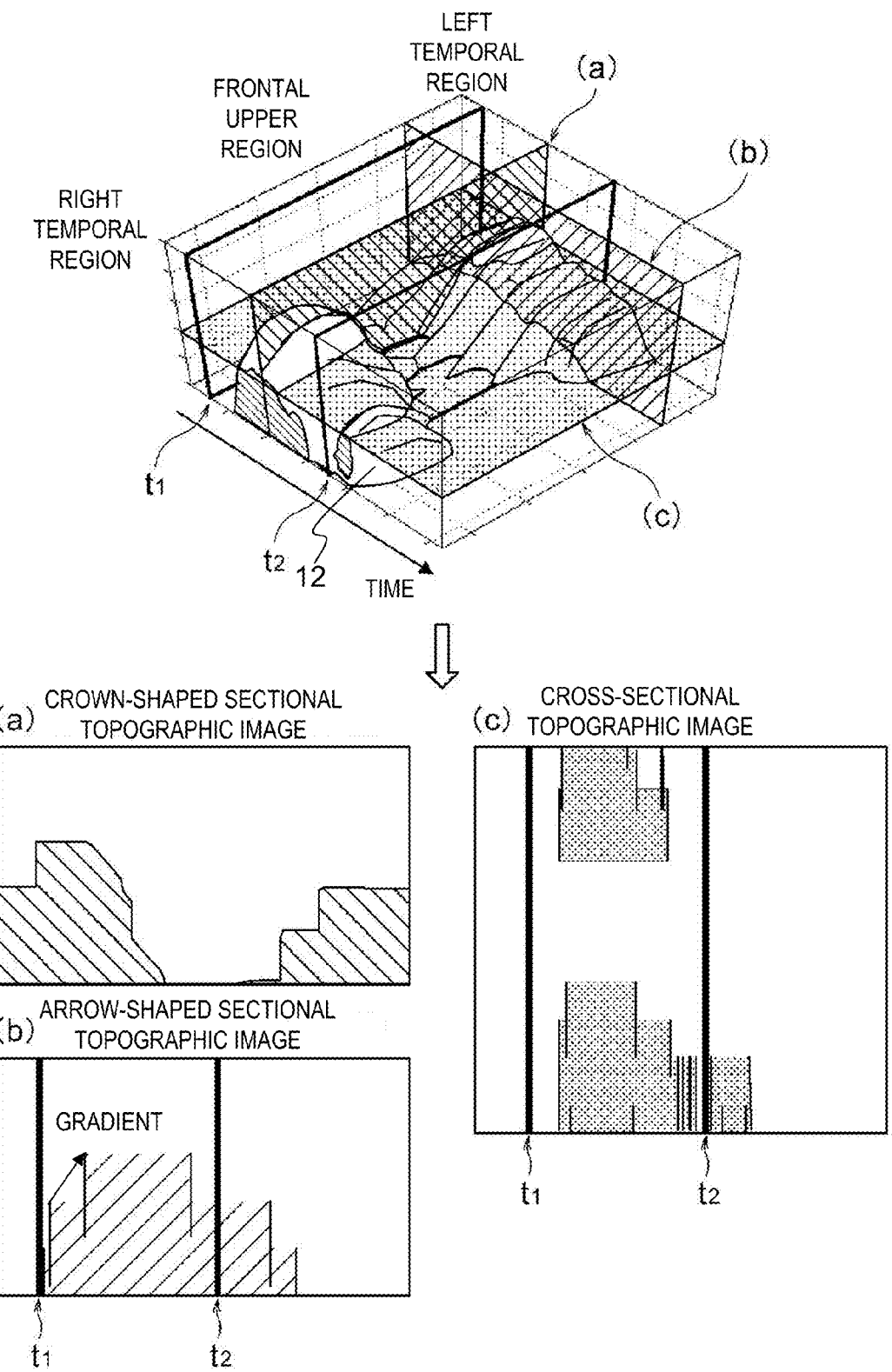
FIG. 11 is a diagram showing examples of three kinds of cross-sectional topographic images extracted from the three-dimensional image of FIG. 4.

Furthermore, any topographic image of the three-dimensional image can be created (cut out) and displayed by the three-dimensional image constructing unit 82. FIG. 11 is a diagram showing an example of three kinds of topographic images extracted from the three-dimensional image of FIG. 4. For example, (a) represents a crown-shaped sectional topographic image perpendicular to the time axis, (b) represents an arrow-shaped sectional topographic image whose section is parallel and vertical to the time axis, and (c) represents a cross-sectional topographic image whose section is parallel and horizontal to the time-axis. a reaction speed caused by the word recall problem can be displayed by the image analyzer 83 on the monitor 9 by calculating the gradient of the three-dimensional image obtained from the three-dimensional image constructing unit 82. Specifically, the image analyzer 83 differentiates the curved line of the boundary between the colored portion and the transparent portion of the arrow-shaped sectional topographic image (cross-sectional image) which is the section parallel and vertical to the time axis shown in FIG. 11(b), thereby measuring the gradient of the arrow-shaped sectional topographic image (cross-sectional image). The gradient is displayed by the image analyzer 83 on the monitor 9. The operator can recognize that the reaction speed is high If the gradient is steep and the reaction speed is low if the gradient is moderate. The arrow-shaped sectional topographic image is an image parallel to the time axis, and the gradient may be measured from the image along the arrows (stream line).

Figure 12:
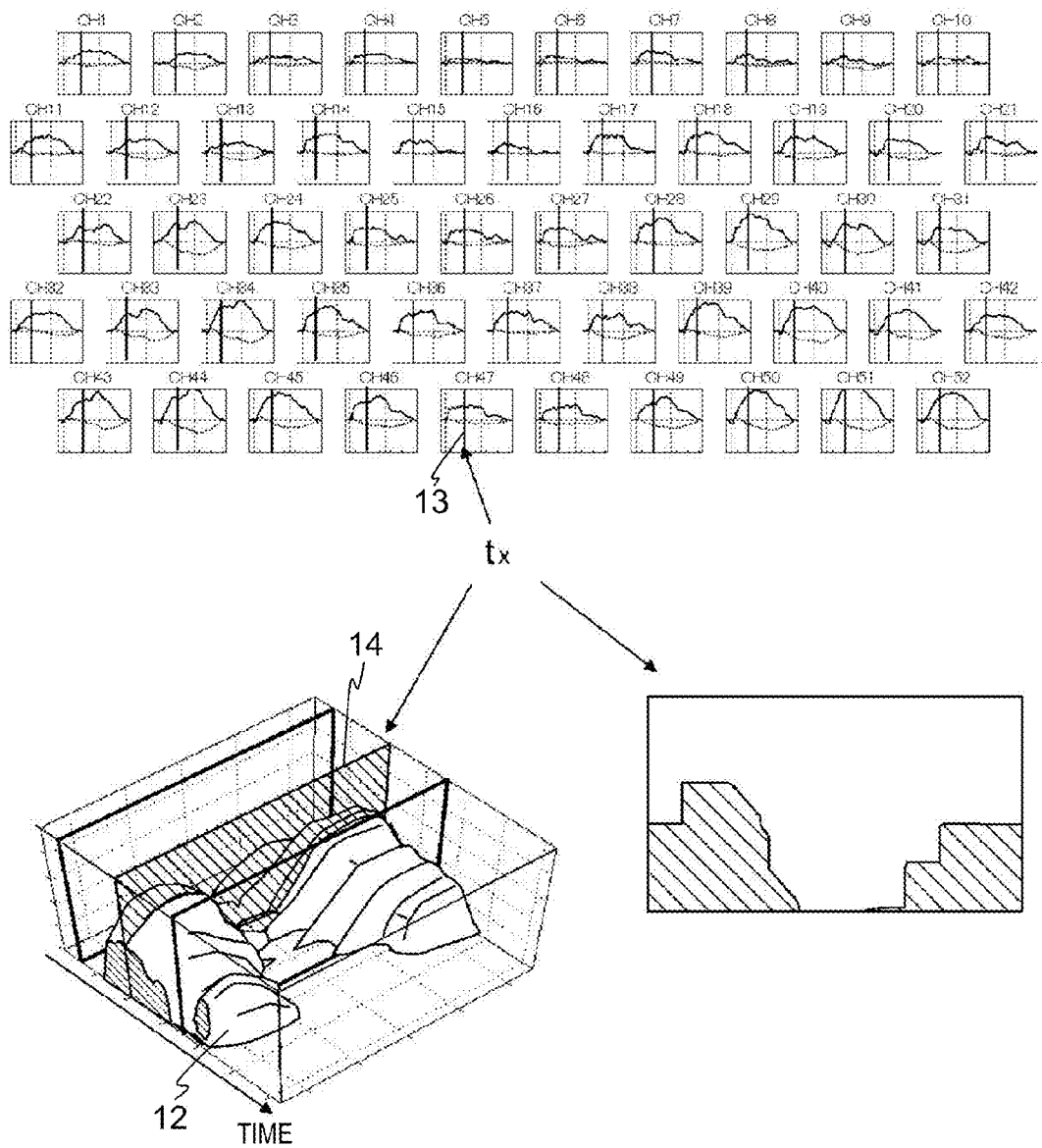
FIG. 12 is a diagram showing an example in which the graph group of FIG. 3, the three-dimensional image of FIG. 4 and the crown-shaped cross-sectional topographic image of FIG. 11 are combined and displayed.

Furthermore, the body mark 10a as shown in FIG. 2, the graph group as shown in FIG. 3, the three-dimensional image as shown in FIG. 4 and the sectional image as shown in FIG. 11 can be displayed by the display controller 8 while they are properly combined. For example, FIG. 12 shows an example in which the graph group as shown in FIG. 3, the three-dimensional image of FIG. 4 and the crown-shaped topographic image shown in FIG. 11 are combined and displayed. The crown-shaped sectional topographic image of FIG. 12 represents a two-dimensional topographic image representing the hemoglobin concentration distribution at a time tx indicated by the operator. For example, a time bar 13 representing the time tx is displayed in each graph by the graph group constructing unit 84. A measurement time plane 14 as a time mark representing the time tx is displayed by the three-dimensional image constructing unit 82 in the three-dimensional image. Accordingly, it is easy to consider the graph group, the three-dimensional image and the sectional image while comparing them.

Furthermore, the display controller 8 moves the measurement time plane 14 along the time-axis direction at a predetermined speed, and also it can read out the position of the time bar 13 within each graph and the two-dimensional topographic image from the image storage unit 81, and continuously vary them in accordance with the position of the measurement time plane 14.

In the biological optical measurement apparatus, the time information is combined with the two-dimensional topographic image representing the spatial information (the information within the measurement plane) to perform a three-dimensional display. Accordingly, the visual recognition of the time variation of the measurement result information can be facilitated, and thus the efficiency of identifying a disease can be enhanced.

In order to check the temporal behavior of the variation amount of the hemoglobin concentration, it is necessary to repetitively see a moving picture in which a two-dimensional topographic image is time-varied or image from the graph group as shown in FIG. 12. However, according to the biological optical measurement apparatus of the embodiment, the time-variation of the hemoglobin concentration at all the measurement positions can be easily recognized by the three-dimensional image (three-dimensional topographic image).

Furthermore, when the measurement result is printed to analyze it or explain it to an object, in the conventional instrument, it is possible only to select one or several characteristic two-dimensional topographic images or select a graph group as shown in FIG. 12, and thus it is difficult to analyze or explain the time-variation of hemoglobin concentration. On the other hand, according to the biological optical measurement apparatus of this embodiment, by printing the three-dimensional image, the analysis and explanation of the time-variation of the hemoglobin concentration can be easily performed.

Here, the three-dimensional image shown in FIG. 10 is an example of an image obtained when the word recall problem is executed on a healthy object, and it can be recognized that oxygenated hemoglobin starts to increase from the frontal lower region at the same time as the start (t1) of the word recall problem and then the increase of oxygenated hemoglobin also expands to the right and left temporal regions.

Figure 13:
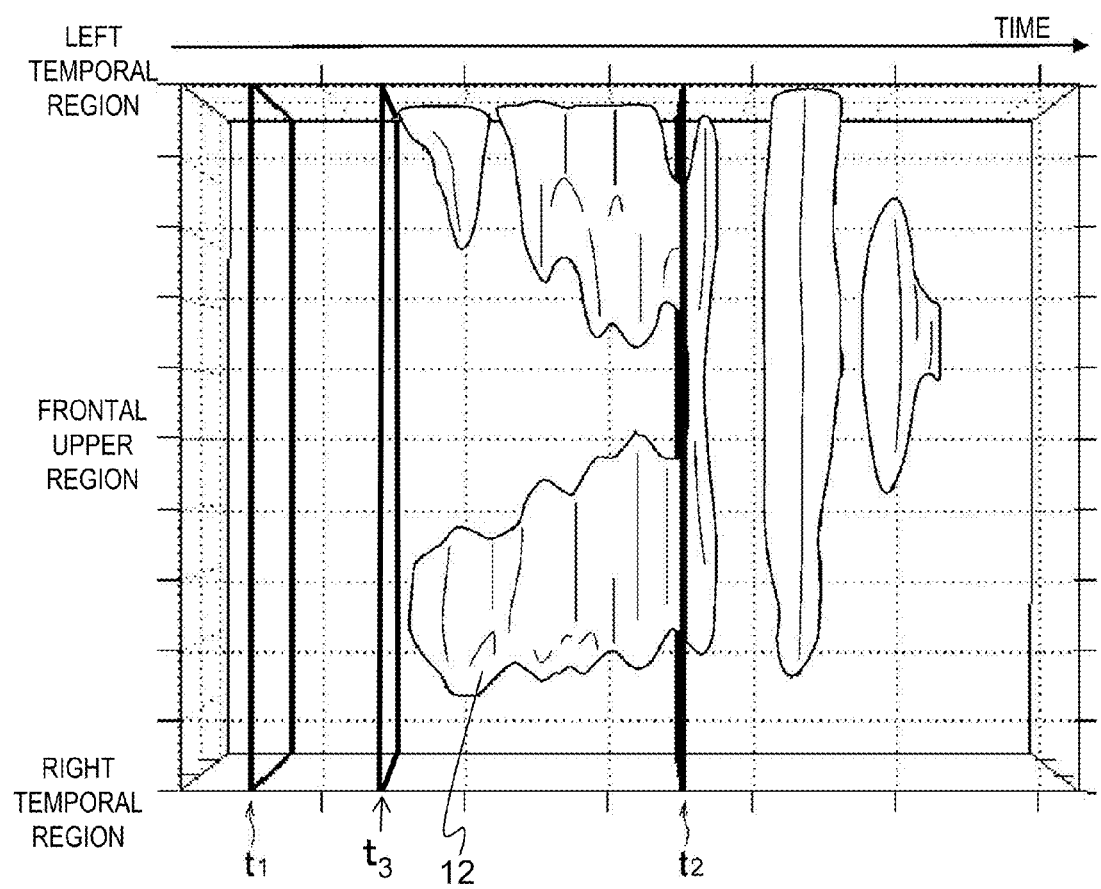
FIG. 13 is a diagram showing an example in which measurement result information of an object having schizophrenia is displayed as a three-dimensional image.

On the other hand, FIG. 13 is a diagram showing an example in which measurement result information of an object with schizophrenia is displayed as a three-dimensional image. In this example, it can be recognized that oxygenated hemoglobin starts to increase from the right and left temporal regions with a time lag from the start (t1) of the word recall problem and after the end (t2) of the word recall problem, oxygenated hemoglobin increases in the frontal region and the right and left temporal regions again.

Figure 14:
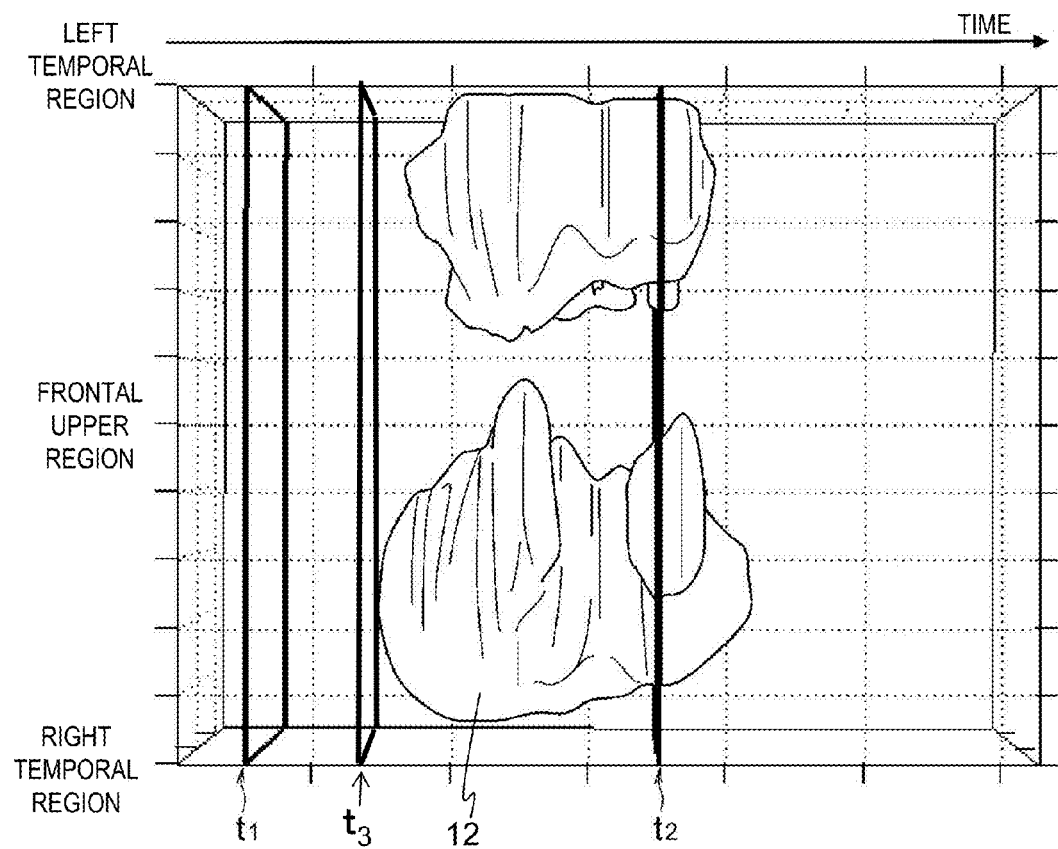
FIG. 14 is a diagram showing an example in which measurement result information of a depressive object is displayed as a three-dimensional image.

Furthermore, FIG. 14 is a diagram showing an example in which the measurement result information of a depressed object is displayed as a three-dimensional image. In this example, it can be recognized that oxygenated hemoglobin starts to increase from the right and left temporal regions with a time lag from the start (t1) of the word recall problem, but no variation occurs in oxygenated hemoglobin concentration after the end (t2) of the word recall problem.

As described above, a feature which is clearly different from that of the healthy object appears in the three-dimensional image of the measurement result information every disease. At this time, the image analyzer 83 can display the reaction start time caused by the word recall problem by measuring the increase start time (t3) of oxygenated hemoglobin. Specifically, the image analyzer 83 measures the increase start time (t3) of oxygenated hemoglobin, and calculates the time (t3−t1) of the start time (t1) of the word recall problem from the increase start time (t3) of oxygenated hemoglobin. The image analyzer 83 displays the above time on the monitor 9. The operator can recognize the reaction start time caused by the word recall problem from the above time. Furthermore, the image analyzer 83 may judge "reaction is slow", "schizophrenic object", "depressed object" or the like if the above time is equal to 0.3 second or more, for example, or the image analyzer 83 may judge "reaction is quick", "healthy object" or the like if the above time is equal to 0.3 second or less. As described above, the reaction start time is effective as a disease identification index.

As is apparent from the three-dimensional images of FIG. 10 and FIG. 14, it is generally known that the volume of the three-dimensional image of the healthy object is larger than the volume of the three-dimensional image of the depressed object. The image analyzer 83 measures the volume of the three-dimensional image of the measurement result information. The measurement of the volume mainly uses the integral calculus or the like. The image analyzer 83 classifies the types of "healthy object" and "depressed object", for example, based on the measured volume. Furthermore, the image analyzer 83 may classify the types by compositely using the reaction start time and the volume of the three-dimensional image.

The interpolation method is not limited to a specific one. For example, linear interpolation, spline interpolation or the like may be used. In the first embodiment, the three-dimensional image is created by the spline interpolation.

Furthermore, the number of channels of measurement points is not limited to a specific one.

Still furthermore, the measurement region may be the whole of the head portion. In this case, the measurement area may be divided into plural blocks, and a block to be displayed may be selected on the screen so that the three-dimensional image corresponding to the block is displayed.

The invention claimed:
1. A biological optical measurement apparatus comprising:
an applied unit having plural light irradiating probes for applying light to an object and plural light detecting probes for detecting light returning from the object, and worn by the object;
a measuring unit for measuring an amount of light detected by the light detecting probes;

a two-dimensional image constructing unit for constructing two-dimensional topographic images from the measurement result of the detected light amount;

a monitor for displaying the two-dimensional topographic images; and a three-dimensional image constructing unit for making the two-dimensional topographic images correspond to measurement positions and superposing the two-dimensional topographic images in order of measurement time to thereby construct a three-dimensional image, the thus-constructed three-dimensional image being displayed on the monitor, wherein the three-dimensional image constructing unit can set a threshold value of the measurement result information, and wherein display/non-display of the measurement result information can be selected with the set threshold value as a boundary.

2. The biological optical measurement apparatus according to claim 1, further comprising a storage unit for storing the two-dimensional topographic images, wherein the three-dimensional image constructing unit constructs the three-dimensional image by superposing the two-dimensional topographic images stored in the storage unit.

3. The biological optical measurement apparatus according to claim 2, wherein the two-dimensional topographic images are read out from the storage unit, and displayed on the monitor together with the three-dimensional image.

4. The biological optical measurement apparatus according to claim 3, wherein the three-dimensional image constructing unit moves the time mark along a time-axis direction at a predetermined speed, and continuously changes the content of the two-dimensional topographic image in connection with the position of the time mark.

5. The biological optical measurement apparatus according to claim 2, wherein the three-dimensional image constructing unit adds the three-dimensional image with a time mark representing the time corresponding to the two-dimensional topographic image to display the three-dimensional image on the monitor.

6. The biological optical measurement apparatus according to claim 1, wherein the three-dimensional image constructing unit creates the three-dimensional image while interpolating adjacent measurement result information with respect to the measurement position and the measurement time.

7. The biological optical measurement apparatus according to claim 1, wherein a site at which a variation amount of hemoglobin concentration as the measurement result is equal to a threshold value or more is color-displayed as an activated portion within the three-dimensional image and a site at which the variation amount of the hemoglobin concentration is less than the threshold value is made transparent by the three-dimensional image constructing unit.

8. The biological optical measurement apparatus according to claim 7, wherein the activated portion can be displayed by the three-dimensional image constructing unit at a predetermined degree of transparency.

9. The biological optical measurement apparatus according to claim 1, wherein the three-dimensional image constructing unit displays arrows for linking peak positions of the hemoglobin concentration at respective times within the three-dimensional image.

10. The biological optical measurement apparatus according to claim 1, further comprising a graph group constructing unit for constructing a graph representing the time variation of the measurement value at each measurement position, a group of graphs arranged in connection with the measurement positions being displayed on the monitor together with the three-dimensional image.

11. The biological optical measurement apparatus according to claim 1, wherein the three-dimensional image constructing unit displays the three-dimensional image of any angle on the monitor.

12. The biological optical measurement apparatus according to claim 1, wherein the three-dimensional constructing unit displays the three-dimensional image in a time zone from the start of a problem to the end of the problem with a color different from the colors of the three-dimensional image of a time zone regions of before the start of the problem and after the end of the problem.

13. The biological optical measurement apparatus according to claim 1, wherein the three-dimensional image constructing unit shades the activated portion of the three-dimensional image and displays the three-dimensional image on the monitor.

14. The biological optical measurement apparatus according to claim 1, wherein the three-dimensional image constructing unit creates any sectional image of the three-dimensional image, and displays the sectional image on the monitor.

15. The biological optical measurement apparatus according to claim 1, further comprising an image analyzer for measuring from the three-dimensional image a time at which increase of oxygenated hemoglobin starts, wherein the time is displayed on the monitor.

16. The biological optical measurement apparatus according to claim 15 wherein the image analyzer measures a gradient of the three-dimensional image.

17. biological optical measurement apparatus according to claim 15, wherein the image analyzer measures the volume of the three-dimensional image.

* * * * *